(12) United States Patent
Goldbard et al.

(10) Patent No.: US 7,338,773 B2
(45) Date of Patent: Mar. 4, 2008

(54) MULTIPLEXED ASSAYS OF CELL MIGRATION

(75) Inventors: Simon Goldbard, San Jose, CA (US); Ilya Ravkin, Palo Alto, CA (US); Oren E. Beske, Sunnyvale, CA (US)

(73) Assignee: Millipore Corporation, Billerica, MA (US)

( * ) Notice: Subject to any disclaimer, the term of this patent is extended or adjusted under 35 U.S.C. 154(b) by 175 days.

(21) Appl. No.: 10/842,954

(22) Filed: May 10, 2004

(65) Prior Publication Data

US 2005/0009113 A1 Jan. 13, 2005

Related U.S. Application Data

(63) Continuation-in-part of application No. 10/282,940, filed on Oct. 28, 2002.

(60) Provisional application No. 60/348,027, filed on Oct. 26, 2001, provisional application No. 60/421,280, filed on Oct. 25, 2002, provisional application No. 60/469,508, filed on May 8, 2003, provisional application No. 60/503,406, filed on Sep. 15, 2003, provisional application No. 60/523,747, filed on Nov. 19, 2003, provisional application No. 60/537,454, filed on Jan. 15, 2004.

(51) Int. Cl.
*G01N 33/567* (2006.01)

(52) U.S. Cl. .................................... 435/7.21

(58) Field of Classification Search ............... 435/7.21, 435/0.4, 7.2, 283.1, 287.1–287.3, 287.7–287.9, 435/288.4–288.7; 436/514; 472/246, 244
See application file for complete search history.

(56) References Cited

U.S. PATENT DOCUMENTS

| | | | |
|---|---|---|---|
| 4,053,362 A | 10/1977 | Sforza | |
| 4,980,293 A | 12/1990 | Jeffs | |
| 5,120,503 A | 6/1992 | Hinckley et al. | |
| 5,130,105 A | 7/1992 | Carter et al. | |
| 5,134,064 A | 7/1992 | Nordlund | |
| 5,141,718 A | 8/1992 | Clark | |
| 5,593,875 A | 1/1997 | Wurm et al. | |
| 5,830,411 A | 11/1998 | Martinell Gisper-Sauch | |
| 5,916,526 A | 6/1999 | Robbins | |
| 5,989,835 A | 11/1999 | Dunlay et al. | |
| 6,027,695 A | 2/2000 | Oldenburg et al. | |
| 6,039,804 A | 3/2000 | Kim et al. | |
| 6,168,914 B1 * | 1/2001 | Campbell et al. | 435/4 |
| 6,232,066 B1 | 5/2001 | Felder et al. | |
| 6,238,869 B1 | 5/2001 | Kris et al. | |
| 6,406,845 B1 | 6/2002 | Walt et al. | |
| 6,429,027 B1 | 8/2002 | Chee et al. | |
| 6,458,533 B1 | 10/2002 | Felder et al. | |
| 6,699,665 B1 | 3/2004 | Kim et al. | |
| 6,913,732 B2 | 7/2005 | Sha et al. | |

FOREIGN PATENT DOCUMENTS

| | | |
|---|---|---|
| JP | 1-144970 | 6/1989 |
| WO | WO 98/50782 | 11/1998 |
| WO | WO 00/63419 | 10/2000 |
| WO | WO 02/37944 | 5/2002 |
| WO | WO 02/48676 | 6/2002 |
| WO | WO 03/036265 | 5/2003 |

OTHER PUBLICATIONS

Arrays of Arrays for High-Throughput Gene Expression Profiling, Zarrinkar et al., *Genome Research*, vol. 11, No. 7, pp. 1256-1261, Jul. 2001.
SearchLight™ Protein Array Technology, Pierce Boston Technology Center, internet pp. 1-2, printed Oct. 21, 2002.
Microtiter Format for Simultaneous Multianalyte Detection and Development of a PCR—Chemiluminescent Enzyme Immunoassay for Typing Human Papillomavirus DNAs, Roda et al., *Clinical Chemistry*, vol. 48, No. 10, pp. 1654-1660, Oct. 2002.
Membrane Array Technology for Drug Discovery, Groves, *Drug Discovery & Development*, vol. 5, No. 4, pp. 606-612, 2002.
*Multiplexed Chemiluminescent Assays in ArrayPlates™ for High-Throughput Measurement of Gene Expression*, Martel et al., High Throughput Genomics, Inc., pp. 1-9, undated.
*A New Technology Platform for Drug Discovery*, Glezer et al., Meso Scale Discovery, pp. 1-9, undated.
*Ultra-High Throughput SNP Genotyping for Pharmacogenetics and Drug Discovery*, Zhao et al., Orchid BioSciences, Inc., p. 1, undated.

* cited by examiner

*Primary Examiner*—Ann Yen Lam
(74) *Attorney, Agent, or Firm*—Hamilton, Brook, Smith & Reynolds, P.C.

(57) ABSTRACT

Systems, including methods, apparatus, compositions, and kits, for multiplexed assay of cell migration with subdivided cell holders and/or microplates.

11 Claims, 4 Drawing Sheets
(3 of 4 Drawing Sheet(s) Filed in Color)

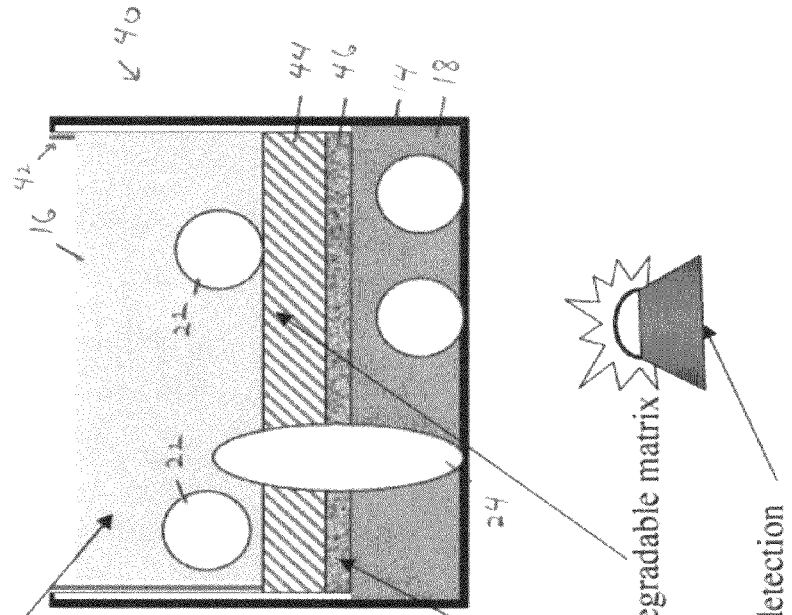
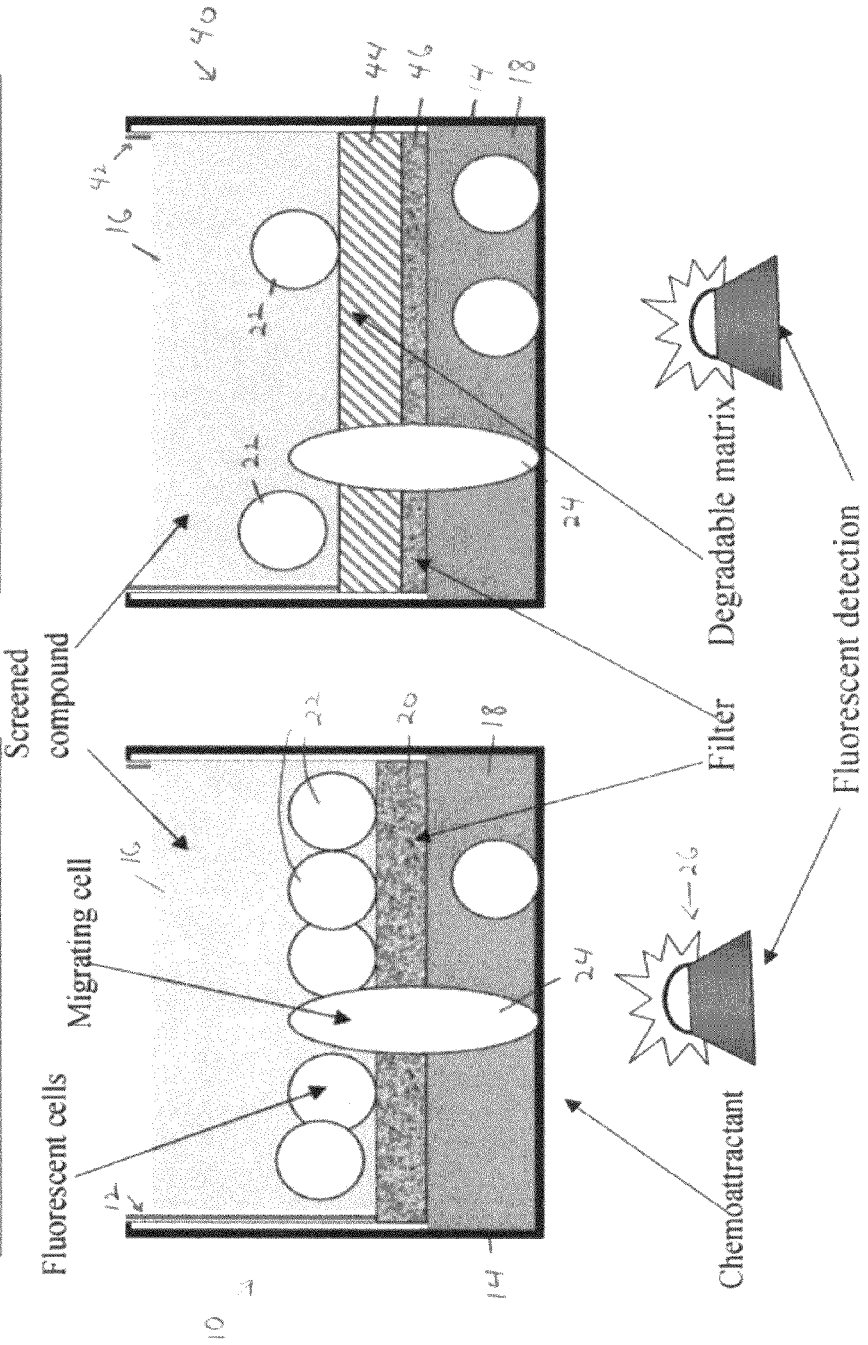

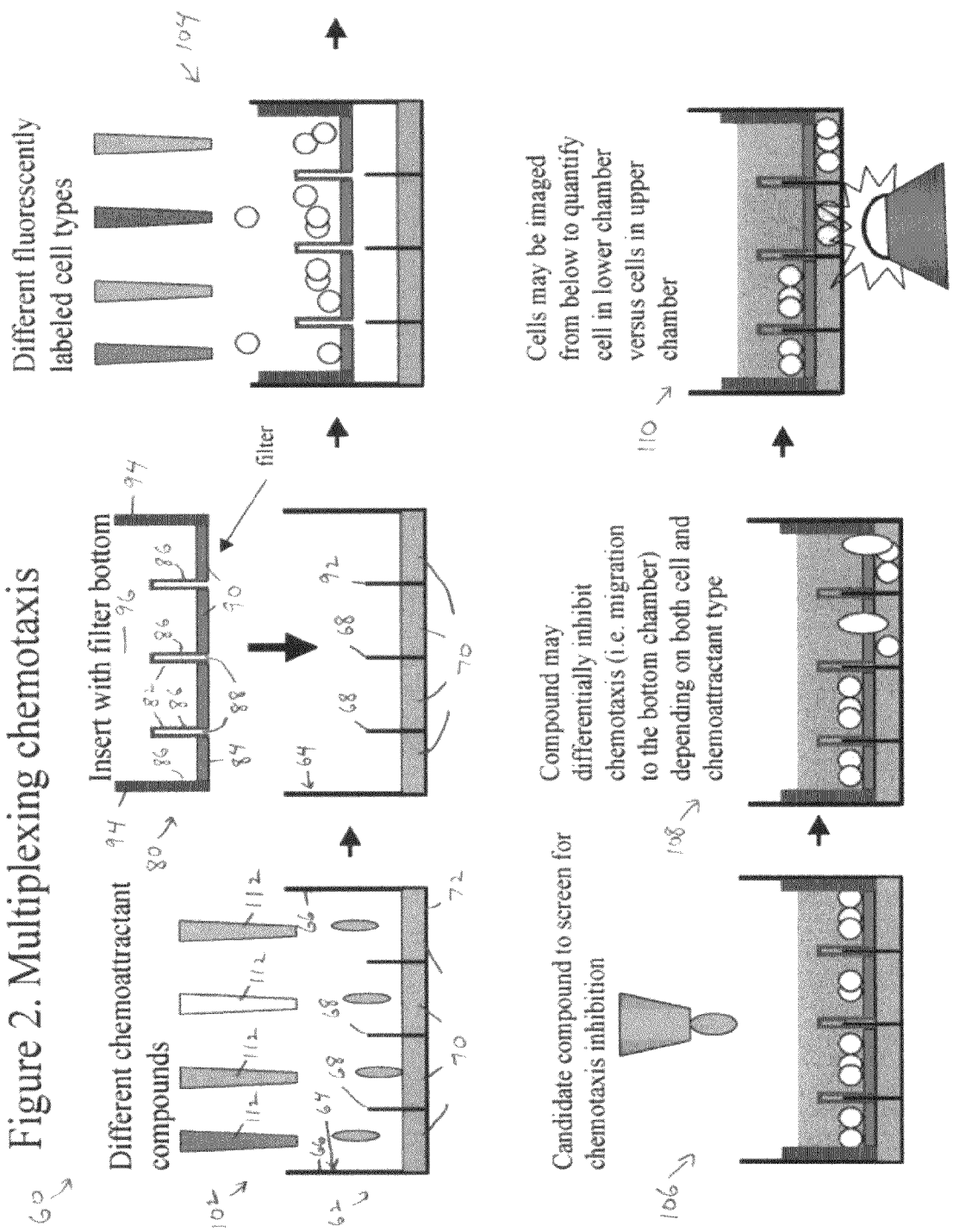

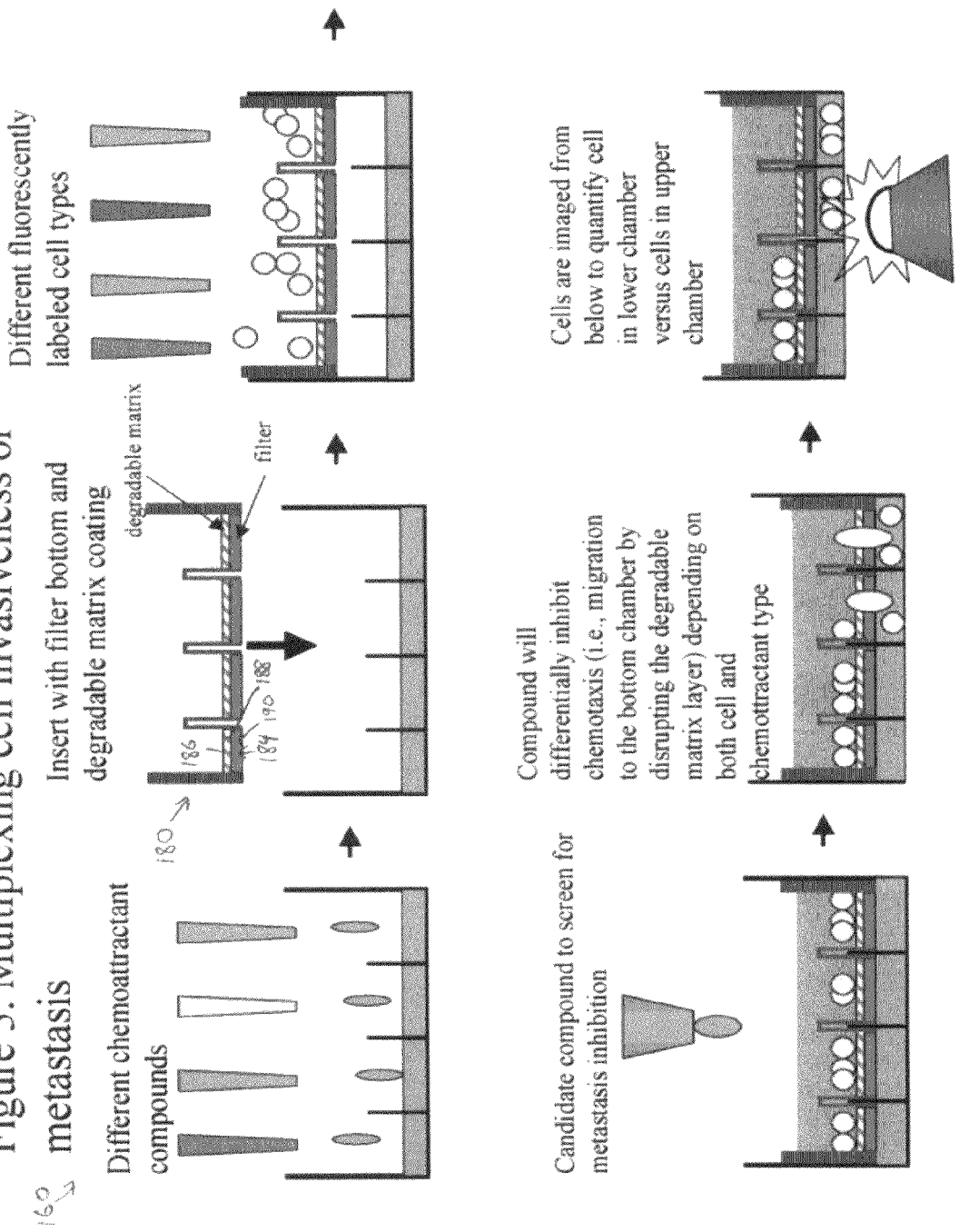

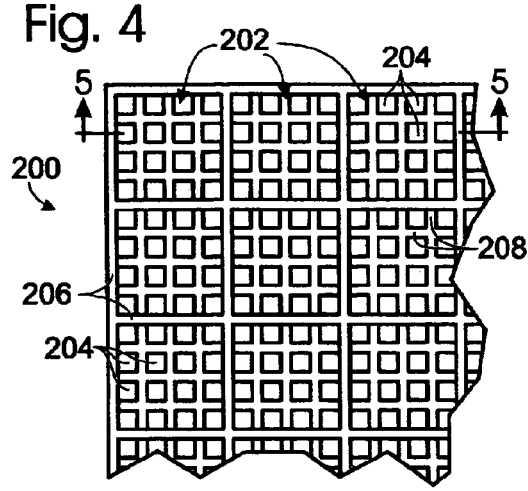
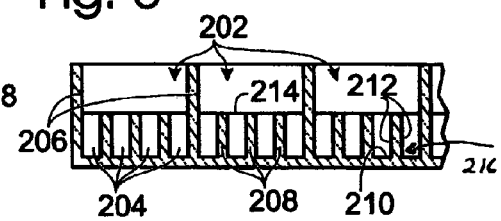
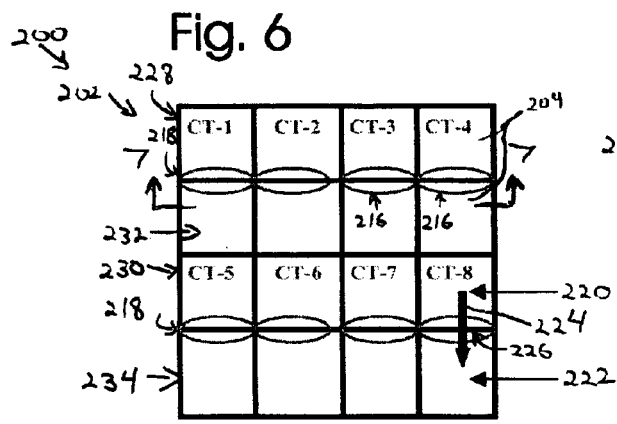
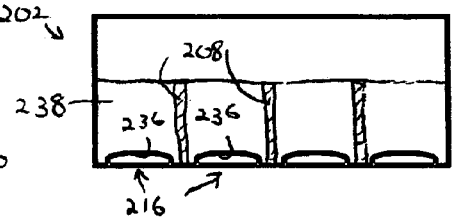

MULTIPLEXED ASSAYS OF CELL MIGRATION

CROSS-REFERENCE TO PRIORITY APPLICATIONS

This application is a continuation-in-part of U.S. patent application Ser. No. 10/282,940, filed Oct. 28, 2002. This application is also based upon and claims benefit under 35 U.S.C. § 119(e) of U.S. Provisional Patent Application Ser. No. 60/469,508, filed May 8, 2003.

U.S. patent application Ser. No. 10/282,940, in turn, claims priority under 35 U.S.C. § 119(e) from U.S. Provisional Patent Application Ser. No. 60/348,027, filed Oct. 26, 2001, and U.S. Provisional Patent Application Ser. No. 60/421,280, filed Oct. 25, 2002.

The above-identified U.S. and provisional priority patent applications are all incorporated herein by reference in their entirety for all purposes.

CROSS-REFERENCE TO RELATED APPLICATIONS

This application incorporates by reference in their entirety for all purposes the following U.S. patent applications: Ser. No. 09/549,970, filed Apr. 14, 2000; Ser. No. 09/694,077, filed Oct. 19, 2000; Ser. No. 10/120,900, filed Apr. 10, 2002; Ser. No. 10/238,914, filed Sep. 9, 2002; Ser. No. 10/273,605, filed Oct. 18, 2002; Ser. No. 10/282,904, filed Oct. 28, 2002; Ser. No. 10/282,940, filed Oct. 28, 2002; Ser. No. 10/382,796, filed Mar. 5, 2003; Ser. No. 10/382,797, filed Mar. 5, 2003; Ser. No. 10/382,818, filed Mar. 5, 2003; Ser. No. 10/407,630, filed Apr. 4, 2003; Ser. No. 10/444,573, filed May 23, 2003; Ser. No. 10/445,291, filed May 23, 2003; and Ser. No. 10/713,866, filed Nov. 14, 2003.

This application also incorporates by reference in their entirety for all purposes the following U.S. provisional patent applications: Ser. No. 60/503,406, filed Sep. 15, 2003; Ser. No. 60/523,747, filed Nov. 19, 2003; and Ser. No. 60/537,454, filed Jan. 15, 2004.

This application also incorporates by reference in their entirety for all purposes the following PCT patent applications: Ser. No. PCT/US00/10181, filed Apr. 14, 2000, and published as Publication No. WO 00/63419 on Oct. 26, 2000; Ser. No. PCT/US01/51413, filed Oct. 18, 2001, and published as Publication No. WO 02/37944, May 16, 2002; Ser. No. PCT/US02/33350, filed Oct. 18, 2002; and Ser. No. PCT/US02/34699, filed Oct. 28, 2002.

BACKGROUND OF THE INVENTION

Cell migration is fundamental to many biological processes, including development, inflammation, wound healing, tissue remodeling, and metastasis (cancer). However, the complexity of studying cell migration in vivo has made it difficult to identify agonists and antagonists of cell migration. As a result, development of high-throughput in vitro assay systems for cell migration may be an important step toward discovering drugs that modulate migration.

SUMMARY OF THE INVENTION

The invention provides systems, including methods, apparatus, compositions, and kits, for multiplexed assay of cell migration with subdivided cell holders and/or microplates.

BRIEF DESCRIPTION OF THE DRAWINGS

The patent or application file contains at least one drawing executed in color. Copies of this patent or patent application publication with color drawings will be provided by the Office upon request and payment of the necessary fee.

FIG. 1A is a schematic sectional view of an assembly that includes a migration-permissive cell holder placed in a microplate well, with the assembly being used to perform a migration assay for cell movement through a porous membrane and toward a chemoattractant.

FIG. 1B is a schematic sectional view of an assembly that includes a migration-permissive cell holder placed in a microplate well, with the assembly being used to perform an invasiveness assay for cell movement through a biological matrix and a porous membrane, and toward a chemoattractant.

FIG. 2 is a schematic view of a multiplexed migration assay for cell movement through a porous membrane and toward a set of different chemoattractants, performed with a migration-permissive, subdivided cell holder placed in a subdivided microplate well, in accordance with aspects of the invention.

FIG. 3 is a schematic View of a multiplexed invasiveness assay for cell movement through a biological matrix and porous membrane and toward a set of different chemoattractant compounds, performed with a migration-permissive, subdivided cell holder placed in a subdivided microplate well, in accordance with aspects of the invention.

FIG. 4 is a fragmentary, top plan view of an exemplary sample holder for cell migration assays, with a two-tiered hierarchy of sample compartments in which individual wells are subdivided into sub-wells, in accordance with aspects of the invention.

FIG. 5 is a sectional view of the sample holder of FIG. 4, taken generally along line 5-5 of FIG. 4, in accordance with aspects of the invention.

FIG. 6 is a somewhat schematic, top plan view of one of the wells of the sample holder of FIG. 4, with the well holding a plurality of cell types in different sub-wells of the well, in accordance with aspects of the invention.

FIG. 7 is a sectional view of the well of FIG. 6, taken generally along line 7-7 of FIG. 6, in accordance with aspects of the invention.

DETAILED DESCRIPTION

The invention provides systems, including methods, apparatus, compositions, and kits, for multiplexed assay of cell migration through and/or within subdivided cell holders. The cell holders may be permeable inserts. The permeable inserts may be placed into receiving compartments, such those defined by microplate wells, to conduct the assays. The cell holders may be configured to be permeable to cells. The cell holders may be nonselectively permeable, that is, permissive for movement of substantially migrating cells of any size (or of less than a predefined size). Nonselectively permeable cell holders may be employed to conduct, for example, chemotaxis assays. Alternatively, the cell holders may be selectively permeable, that is, permissive for movement of migrating cells capable of modifying the cell holders to allow passage of the cells, such as by degradation of a portion of the cell holders. Selectively permeable cell holders may be employed to conduct, for example, invasiveness assays, which may be a measure of metastatic potential.

Alternatively, or in addition, the subdivided cell holders may include sample holders such as microplates. The microplates may include compartments, such as wells and/or sub-wells, defined by a floor and side walls. The side walls may include an opening that permits cell migration and restricts passive movement of cells, such as by diffusion. The opening may be a slit disposed at the base of a side wall(s). Openings may be arranged to separate pairs of wells or sub-wells. The use of subdivided cell holders for multiplexed cell migration assays may enable a greater number of cell types, chemoattractants (cell-attractive materials), migration agonists, and/or migration antagonists to be screened more efficiently.

Each subdivided cell holder or permeable insert may define an array of insert sub-compartments configured to hold fluid and cells. A region of each insert sub-compartment, such as a bottom wall or bottom portion, may include a porous matrix. The porous matrix may enable fluid communication between the insert sub-compartment and a receiving compartment opposing the insert sub-compartment across the porous matrix, and may be cell permeable. Accordingly, cells may be placed in each insert sub-compartment and tested for their ability to migrate into and/or across the porous matrix to the receiving compartment. A known or candidate cell-attractive material may be placed in the receiving compartment to promote cell migration and/or to test promotion of migration.

The receiving compartment may be defined by any suitable vessel that can hold fluid and receive migratory cells. In some embodiments, the receiving compartment may be defined by a well of a microplate configured to at least partially receive the subdivided cell holder. The well may define a single compartment. Accordingly, the assays may measure migratory loss of cells from each insert sub-compartment and/or localization of the cells to sub-regions of the well opposing the insert sub-compartments.

Alternatively, the well may define a plurality of well sub-compartments or sub-wells. The sub-wells may correspond at least substantially to the insert sub-compartments in number and relative position, to define an array that corresponds to the array defined by the insert sub-compartments. The sub-wells may be addressable in fluid isolation or fluid communication according to the level of fluid added to the sub-wells and/or well, as described in more detail in U.S. patent application Ser. No. 10/282,940, filed Oct. 28, 2002, which is incorporated herein by reference. Accordingly, the assays may measure migration of cells from each insert sub-compartment into a corresponding sub-well underlying and/or apposed to the sub-compartment.

Fluid contact between the fluid contents of the sub-wells and the insert sub-compartments may be determined by a porous matrix. The porous matrix may be disposed at or adjacent the bottom of each insert sub-compartment. The porous matrix may be segmented into porous segments localized to individual insert sub-compartments to enable each insert sub-compartment to make isolated fluid contact with an underlying sub-well. Accordingly, each porous segment may be received in a corresponding sub-well. Lower side walls of the subdivided cell holder, extending generally upward from the porous segments, may be spaced to define a recess configured to receive inner walls of the well (which subdivide the well into sub-wells). Furthermore, each sub-well may hold the same or a different known or candidate cell-attractive material, to enable each insert sub-compartment to be exposed to the same or different cell-attractive material emanating from the sub-well or well and into the subdivided cell holder.

Similar to a subdivided well, the subdivided cell holder may be configured to provide adjustable fluid communication of the insert sub-compartments based on the level of fluid placed in the subdivided cell holder. The lower side walls of the subdivided cell holder may be connected to upper side walls that define a shared compartment adjoining and above the insert sub-compartments. Thus, the insert sub-compartments may be addressed individually with smaller amounts of fluid, or overfilled to provide fluid communication above the lower side walls of the insert sub-compartments.

Migration assays with the subdivided inserts may use any suitable set of cells, cell-attractive materials, and/or known or candidate migration modulators. The assays may use the same type(s) of cells in each insert sub-compartment or different types of cells in some or all of the insert sub-compartments. Accordingly, the cells may be placed separately in each of the insert sub-compartments or a suspension of cells may be addressed to all of the sub-compartments by overfilling the lower side walls, among others. The assays may use known or candidate cell-attractive materials disposed in the receiving compartment and/or the insert sub-compartments. For example, a single cell-attractive material (or set of such materials) may be in fluid communication with a plurality of insert sub-compartments, or different cell-attractive materials may be in fluid with different insert sub-compartments. In some embodiments, the insert sub-compartments may hold different cell types with different cell-attractive materials opposed to each sub-compartment in separate sub-wells of the receiving compartment. The assays may place known or candidate migration modulators, that is, agonists or antagonists of migration, within the sub-compartments of the subdivided cell holder. The same or different migration modulators may be placed in each insert sub-compartment, for example, by placing the insert sub-compartments in fluid communication or isolation, respectively, above the lower side walls.

Cell-attractive materials and/or migration modulators may be any suitable compound, complex, polymer, mixture, or extract. In some embodiments, the cell-attractive materials (and/or migration modulators) may be chemokines, defined by a superfamily of small (8-10 kDa) cytokines. Exemplary chemokines may include, but are not limited to, IL-8, GRO, RANTES, leukotriene B4, stromal derived factor 1, MCP1-4, KC, MIP-2, ENA-78, GCP-2, PBP/CTAPIII/b-TG/NAP-2, IP-10, eotaxin, I-309/TCA3, HCC-1, C10, or lymphotactin. In some embodiments, the cell-attractive materials (and/or migration modulators) may be synthetic compounds, such as formyl methionyl leucyl phenylalanine.

Any suitable cells may be used for the migration assays. The cells may be hematopoietic cells (such as macrophages, eosinophils, lymphocytes, basophils, neutrophils, etc.) or non-hematopoietic cells such as fibroblasts, smooth muscle cells, keratinocytes, or melanocytes.

The migration assays described herein may enable performance of a greater number of cell migration assays with fewer experimental manipulations. Further aspects of the invention are described below in the examples.

EXAMPLES

The following examples describe selected aspects and embodiments of the invention, including devices and methods for multiplexed analysis of cell migration in subdivided microplate wells. These examples are included for illustration and are not intended to limit or define the entire scope of the invention.

Example 1

Singleplexed Assays for Measuring Cell Migration in Microplate Wells

This example illustrates a device for singleplexed assay of cell migration in microplate wells; see FIGS. 1A and 1B.

FIG. 1A shows an assembly 10 configured for measuring cell migration in vitro in response to a chemoattractant. Assembly 10 includes a permeable chemotaxis insert 12 that is received by a well 14. The chemotaxis insert defines an upper compartment 16 for holding fluid, and the well defines a lower compartment 18. These two compartments are connected fluidly by a porous matrix or filter 20 having pores large enough to permits cells to pass through the filter.

A migration assay may be performed with assembly 10 using cells and a chemoattractant. Cells 22 may be placed in upper compartment 16, and the chemoattractant may be placed in the lower compartment 18. The chemoattractant diffuses into the upper compartment through the filter, forming a gradient of chemoattractant. Accordingly, cells 22 that are responsive to this gradient, such as migrating cell 24, may migrate toward increased chemoattractant concentration, into lower compartment 18. The number of cells that migrate into the lower compartment may be measured optically (among other methods), shown at 26. For example, cells may be fluorescently labeled with a dye, so that they are readily detectable, or the cells may be detected without labeling using suitable optics. In some cases, the filter may be optically opaque, so that only migratory cells are visible when imaged from the bottom, and only nonmigratory cells are visible when imaged from the top.

FIG. 1B shows another assembly 40 configured for measuring cell migration in vitro in response to a chemoattractant. However, assembly 40 differs from assembly 10 of FIG. 1A in being configured more particularly to measure cell migration that is invasive. Accordingly, assembly 40 includes a permeable invasiveness insert 42 that is received by well 14. Invasiveness insert 42 also defines upper compartment 16 for holding fluid and the well defines lower compartment 18. However, invasiveness insert 42 fluidly connects these two compartments using a degradable matrix 44, and, optionally, a filter 46, which may be similar to filter 20 of chemotaxis insert 12 (see FIG. 1A). The degradable matrix may include one or more extracellular matrix components, and thus may restrict cell migration unless one or more of the components is degraded (or cut) to provide a path for cell migration.

Example 2

Multiplexed Assays for Cell Migration in Subdivided Microplate Wells

This example illustrates multiplexed assays of cell migration, such as chemotaxis and invasiveness, using subdivided permeable inserts in subdivided microplate wells; see FIGS. 2 and 3.

2A. Variation 1

FIG. 2 shows a method 60 for multiplexed assay of cell migration in a subdivided microplate well.

2A.1 Multiplexed Assay Apparatus

Method 60 may use a microplate 62 having a subdivided well 64. Well 64 may be one of a plurality of subdivided wells in the microplate. Well 64 may include outer walls 66 and inner walls 68. The inner walls may subdivide well 64 into a plurality of sub-wells 70. The outer walls may extend to a greater height above well bottom 72 than the inner walls to allow adjustable fluid communication. In particular, the sub-wells may be in fluid isolation or fluid communication according to the level of fluid in the well. Subdivided wells, sub-wells, and assays with adjustable fluid communication are described in more detail in U.S. patent application Ser. No. 10/282,940, filed Oct. 28, 2002, which is incorporated herein by reference.

Method 60 may further use a subdivided permeable insert 80 configured to be received by well 64. Subdivided insert 80 may include lower side walls 82 connected to a bottom wall 84 to define an array of insert sub-compartments 86 arranged in correspondence with sub-wells 70 of subdivided well 64. Lower side walls 82 may isolate or separate sub-compartments 86 to prevent lateral fluid communication (and/or cell movement) between the sub-compartments through the lower side walls. In addition, lower side walls 82 may define a recess 88 between the side walls. The recess may be generally complementary to inner walls 68 of subdivided well 64 to allow the inner walls to be received by the recess.

Bottom wall 84 may be configured to provide fluid communication between overlying sub-compartments 86 of the subdivided insert and sub-wells 70 of subdivided well 64. Accordingly, bottom wall 84 may include a porous matrix or filter that includes pores large include to allow movement of fluid and cells through the matrix. The bottom wall may be formed as a plurality of spaced segments 90. Spaced segments 90, in conjunction with recess 88, may enable individual fluid communication between each overlying insert sub-compartment 86 and its corresponding underlying sub-well 70 when the subdivided insert is received by the well. In this case, each bottom wall segment 90 (and its associated lower side walls 82 or lower side wall regions) may be received in a separate sub-well 70. Alternatively, bottom wall 84 and/or lower side walls 82 may be configured to allow the insert to be received by the well but to prevent the bottom wall from being received by the sub-wells. In this case, the fully received insert may contact a top surface 92 of inner walls 68.

Well insert 80 may include upper side walls 94 connected to lower side walls 82 and/or bottom wall 84. Upper side walls 94 may extend higher above the bottom wall than the lower side walls, to define an upper compartment 96 that adjoins and fluidly connects insert sub-compartments 86. The upper side walls may define an upper and/or outer perimeter of the subdivided insert to restrict lateral fluid flow from the subdivided insert to the well. Accordingly, insert sub-compartments 86 may be addressed in fluid isolation or in fluid communication based on whether the fluid level in the subdivided insert is above or below the top of the lower side walls. In some embodiments, the subdivided insert may lack an upper side wall.

2A.2 Multiplexed Assay Methods

Method 60 may enable multiplexed analysis of different known or candidate cell-attractive materials, different types of cells, and/or different known or candidate agonists or antagonists of cell migration, among others. The method may include (1) placing cell-attractive materials in sub-wells, shown at 102; (2) placing cells in the subdivided insert, shown at 104; (3) contacting the cell-attractive materials with the insert and adding a candidate agonist or antagonist, shown at 106; (4) incubating to allow cell migration, if any, shown at 108; and (5) sensing cell migration, if any, shown at 110.

Operation 102 may include placing any suitable known or candidate cell-attractive material(s) in sub-wells 70. Each sub-well may receive the same cell-attractive material, at the same or different concentrations. Alternatively, some or all of the sub-wells may receive different cell-attractive materials 112. The fluid level in each sub-well may be below the top of inner walls 68, to enable fluid isolation, or may be above the top, to enable fluid communication (particularly when the same cell-attractive material is being placed in each sub-well).

Operation 104 may include placing any suitable cells in inserts sub-compartments 86. The same or different types of cells may be placed in each insert sub-compartment. Accordingly, the sub-compartments may be addressed separately, in fluid isolation, or together, in fluid communication (particularly when the same type (or types) of cells are placed in each insert sub-compartment). Cells may be unlabeled or may be labeled, for example with a fluorescent dye.

Operation 106 may include contacting the cell-attractive materials with the subdivided insert by placing subdivided insert 80 into well 64. Placing the insert may dispose lower portions of the insert in contact with fluid in the well. In particular, bottom wall 84 may contact fluid carrying the cell-attractive material(s). Based on the fluid level in the well and the structure of the subdivided insert, contact may occur individually within each sub-well through a corresponding bottom wall segment 90, or with fluid of the entire well, among others.

Operation 106 further may include adding any suitable known or candidate agonist or antagonist. Different (or the same) agonists/antagonists may be added to individual insert sub-compartments 86, or the same agonist/antagonist may be added to some or all sub-compartments. When the same agonist/antagonist is added to all sub-compartments, the fluid level in the subdivided insert may be raised above lower side walls 86, or each insert sub-compartment may be addressed individually.

Operation 108 may include incubating the system for any suitable time under any suitable conditions. Suitable times may include less than about two hours, eight hours, overnight, or for about one to two days, among others. Suitable conditions may include ambient conditions or a temperature, humidity, and/or gas composition suitable for culture of the cells used in the assay.

Operation 110 may include sensing cell migration at any suitable time or times and by any suitable optical methods. Exemplary times may include a single time point immediately after operation 108, or a plurality of time points during operation 108 to provide a time course or kinetic measure of migration. Exemplary optical methods may include measuring fluorescence, bioluminescence, absorbance, scattering, differential interference contrast, etc., in a focal plane including the cells. Imaging may be performed below the insert, above the bottom wall of the insert, or both, among others.

2B. Variation 2

FIG. 3 shows another method 160 for multiplexed assay of cell migration in a subdivided microplate well, particularly assay of cell invasiveness. Method 160 may differ from method 60 in the structure of the subdivided inserts used. In particular, method 160 may employ a subdivided invasiveness insert 180 having a bottom wall 184 that includes a degradable matrix 186 (or a potentially degradable matrix to be tested). The degradable matrix may extend between opposing sides of the bottom wall, or, as shown here, may define a layer 188 disposed adjacent a support layer 190. The support layer may be used, for example, to provide structural support and may be disposed above and/or below the degradable matrix. The degradable matrix may be formed of synthetic materials, such as a synthetic material. Alternatively, the degradable matrix may include a biological component(s), particularly one or more extracellular matrix components, such as proteins and/or glycans, among others. Exemplary degradable matrices may be formed of collagen, laminin, entactin, Matrigel, and/or mixtures thereof. The biological component may be derived from a cell or may be a synthetically derived analog of a cell-produced component. Further aspects of extracellular matrix components or mixtures that may be suitable are described in the patent applications listed above under Cross-References and incorporated herein by reference, particularly U.S. patent application Ser. No. 10/382,797, filed May 5, 2003.

Example 3

Selected Embodiments I

This example describes further aspects of the invention. The invention may include multiplexing of chemotaxis and/or invasiveness across compounds, signaling molecules, and/or cell types. For example, by placing different chemoattractants or signaling molecules in the interior wells of a multiwell plate, and then adding an insert (also divided in small wells) with a filter (or a filter with Matrigel) at the bottom, one can now place different cell lines in the top well and observe their migration to the bottom wells (see FIGS. 2 and 3). Moreover, the large well containing both the small wells and the insert, can be filled with a compound that acts on the migration of the cells by promoting it or inhibiting it (again, see FIGS. 2 and 3). This approach may provide a powerful way of multiplexing the activation or inhibition of signaling pathways, across cell lines, and at the same time, may offer a simultaneous screening system for compounds that can promote or inhibit these pathways or mechanisms.

Example 4

Exemplary Microplates for Migration Assays

This example describes exemplary microplates that may be used for performing migration assays with cells and candidate migration regulators; see FIGS. 4-7.

FIGS. 4 and 5 show top plan and sectional views, respectively, of a sample holder or microplate 200 having a hierarchy of wells 202 and sub-wells 204 within each well. Each well 202 is surrounded by an outer wall 206 and subdivided into sub-wells 204 using inner walls or dividers 208 that partition the well into the sub-wells. Each sub-well 204 is configured to hold a sample independently, for example, cells attached to a bottom surface 210 or a side surface 212 of the sub-well, or a sample in suspension or solution held in a volume defined by the sub-well. Inner walls 208 may be lower than outer walls 206 of the well, so that sub-wells 204 may exist either in a state of fluid isolation (when the sample well is only slightly filled, or at least below sub-well top 214) or in a state of fluid communication (when the sample well is nearly filled, or above top 214).

A subset of inner walls 208 may include a migration region 216 through which cells may migrate, generally horizontally, between laterally disposed sub-wells. The migration region may be configured to permit cells to fit through an opening(s) connecting a pair (or more) of sub-wells. The migration region also may be configured to restrict non-migratory cell movement, such as passive movement of cells. Such passive movement may be by fluid flow or diffusion before cells are attached to a surface (for example, when the cells are first added to/plated in a sub-well) and/or after connected cells have detached from the surface.

The migration region may have any suitable position within a well and/or sub-well. The migration region may be disposed adjacent the floor or bottom surface 210 of the well, for example, near the bottom of inner walls 208. The migration region may be a single opening in each inner wall, such as a slit in the inner wall, or may be a plurality of openings in the inner wall, such as a plurality of pores or channels extending through an inner wall of the well between adjacent sub-wells. Each opening may be configured to permit cell migration between a pair of adjacent sub-wells, or may connect three or more adjacent sub-wells.

The opening(s) of each migration region may have any suitable size and shape. Generally, the opening may be wide enough to permit a cell to move through the opening, but narrow enough to substantially reduce passive movement of cells, so that cells in fluid added to one sub-well are not carried through the opening into an adjacent sub-well by fluid flow or diffusion through the opening. In some examples, the opening may be elongate, such as a slit disposed near the bottom of an inner wall and/or near the floor of the well. In some examples, the opening may be an array of openings or pores disposed near the floor of the well. The width of the opening may be determined by the size of the cells being assayed, the thickness of the inner wall in which the opening is formed, the material from which the inner wall is formed, and/or the like. In exemplary embodiments, intended for illustration only, the opening may be about 1-200 micrometers in width (and height).

A migration region in a sample holder may be formed integrally in the sample holder or may be created by another component added to the sample holder. When formed integrally, the migration region may include one or more openings that are formed by removing material from the sample holder (such as by cutting, drilling, ion bombardment, etching, etc.), and/or may be molded into the sample holder.

FIG. 6 shows a somewhat schematic plan view of one of the wells 202 of microplate 200. Migration regions 216 may be disposed to connect adjacent sub-wells 204 of the well. For example, the migration regions, indicated here schematically as ovals, may provide fluid communication between, and thus connect, adjacent pairs of sub-wells. In exemplary embodiments, the migration regions may be formed in every other row (or every other column or other suitable pattern) of inner walls, shown here at 218. In some embodiments, the migration regions may connect wells of a sample holder, rather than, or in addition to, sub-wells. Accordingly, the migration regions may be included in microplates having wells and lacking sub-wells.

Cells may be placed in one of the sub-wells, such as sub-well 220, and then assayed for movement into an adjacent, connected sub-well 222, along migration path 224 and through a corresponding migration region, shown at 226. In the present illustration, alternating rows of sub-wells, shown at 228, 230, have received cell types (CT), indicated as CT-1 to CT-8. The cell types (test cells) may be treated with any suitable known or candidate migration regulator, and then tested for movement to connected rows of sub-wells, shown at 232, 234. The cells may be the same type of cells in each sub-well or may be different types of cells in different sub-wells. The cells in different sub-wells may be treated with the same or different, known or candidate regulators, in fluid isolation or fluid communication.

The connected sub-wells (destination sub-wells), into which the cell types may migrate, may hold fluid, a known or candidate migration regulator, distinguishable cells (different than test cells) or no cells, and/or the like. Migration assays may measure an aspect of cells that enter the destination sub-wells (such as number, density, activity, etc.) and/or an aspect of cells that remain in their original sub-wells.

FIG. 7 shows a somewhat schematic, sectional view of well 202, taken generally along line 7-7 of FIG. 6. Openings (holes) 236 of the migration regions 216 may be defined in transverse inner wall 238. In some examples, the openings may be slits. The slits may have a height (a width) that permits cell migration, but restricts passive movement of cells through the slit (such as by diffusion) before, during, and, and/or after the cells are attached to the surface of the microplate. The openings may be small enough to restrict fluid flow, so that a concentration gradient of a test compound may be formed by placing the test compound in a destination sub-well (and not in the sub-well in which the cells are plated). In this case, connected sub-wells may permit diffusion of the test compound through the opening, but may be in fluid isolation otherwise.

The disclosure set forth above may encompass multiple distinct inventions with independent utility. Although each of these inventions has been disclosed in its preferred form(s), the specific embodiments thereof as disclosed and illustrated herein are not to be considered in a limiting sense, because numerous variations are possible. The subject matter of the inventions includes all novel and nonobvious combinations and subcombinations of the various elements, features, functions, and/or properties disclosed herein. The following claims particularly point out certain combinations and subcombinations regarded as novel and nonobvious. Inventions embodied in other combinations and subcombinations of features, functions, elements, and/or properties may be claimed in applications claiming priority from this or a related application. Such claims, whether directed to a different invention or to the same invention, and whether broader, narrower, equal, or different in scope to the original claims, also are regarded as included within the subject matter of the inventions of the present disclosure.

We claim:

1. A device for performing cell migration assays, comprising an insert configured to be received by a microplate well such that the insert is contained at least partially with the microplate well, the insert including a bottom wall and a plurality of side walls connected to the bottom wall to define an array of discrete fluid compartments, the bottom wall including a porous matrix configured to permit fluid communication and cell migration between each fluid compartment and a lower portion of the microplate well.

2. The device of claim 1, the microplate well being subdivided into sub-wells, wherein the bottom wall of the insert includes a spaced set of bottom wall segments, and wherein each bottom wall segment is configured to be received by a different sub-well.

3. The device of claim 2, the fluid compartments being configured as separate fluid holders, and wherein each fluid holder is configured to be at least partially received by a different sub-well.

4. The device of claim 3, the microplate well being subdivided into sub-wells by inner walls, wherein the side walls of the insert define recessed portions configured to receive at least an upper portion of the inner walls.

5. The device of claim 1, the side walls being lower side walls, wherein the insert includes upper side walls disposed adjacent the lower side walls, the upper side walls defining a shared compartment for holding fluid disposed above and adjoining the array of fluid compartments.

6. The device of claim 1, wherein the porous matrix includes a degradable matrix, the degradable matrix being configured to permit cell migration after modification by cells.

7. The device of claim 6, wherein the degradable matrix includes one or more extracellular matrix components, and wherein the modification includes cutting at least one of the extracellular matrix components.

8. The device of claim 1, wherein the side walls are configured to prevent lateral fluid communication between the fluid compartments.

9. The device of claim 1, wherein the insert is a plurality of connected inserts disposed in correspondence with a plurality of wells of the microplate.

10. The device of claim 1, wherein the insert also includes a handle portion connected to the side walls and configured to extend above the microplate well when the insert is received by the microplate well.

11. The device of claim 1, wherein the bottom wall is at least substantially opaque to visible light.

* * * * *